US007470289B2

(12) United States Patent
Brehm

(10) Patent No.: US 7,470,289 B2
(45) Date of Patent: Dec. 30, 2008

(54) TIBIA COMPONENT AND SLIDING PLATE OF A KNEE-JOINT ENDOPROSTHESIS

(76) Inventor: Peter Brehm, Am Mühlberg 34, 91085 Weisendorf (DE)

( * ) Notice: Subject to any disclaimer, the term of this patent is extended or adjusted under 35 U.S.C. 154(b) by 477 days.

(21) Appl. No.: 10/514,493

(22) PCT Filed: May 12, 2003

(86) PCT No.: PCT/EP03/04936

§ 371 (c)(1), (2), (4) Date: Nov. 15, 2004

(87) PCT Pub. No.: WO03/094804

PCT Pub. Date: Nov. 20, 2003

(65) Prior Publication Data

US 2005/0222686 A1 Oct. 6, 2005

(30) Foreign Application Priority Data

May 14, 2002 (DE) ................................ 102 21 272

(51) Int. Cl.
*A61F 2/38* (2006.01)

(52) U.S. Cl. ................................ 623/20.15; 623/20.32

(58) Field of Classification Search .............. 623/20.15, 623/20.19, 20.21, 20.28, 20.29, 20.32, 20.33, 623/20.34, 23.46
See application file for complete search history.

(56) References Cited

U.S. PATENT DOCUMENTS

| | | | | |
|---|---|---|---|---|
| 5,489,311 | A | 2/1996 | Cipolletti | |
| 6,053,945 | A * | 4/2000 | O'Neil et al. | 623/20.32 |
| 6,090,144 | A | 7/2000 | Letot et al. | |
| 6,099,570 | A * | 8/2000 | Livet et al. | 623/20.21 |

FOREIGN PATENT DOCUMENTS

| | | | |
|---|---|---|---|
| DE | 41 02 509 | A1 | 7/1992 |
| EP | 0 294 298 | B1 * | 5/1991 |
| EP | 0 838 204 | A | 4/1998 |
| EP | 0 904 748 | A | 3/1999 |
| FR | 2 278 389 | A | 11/1997 |

* cited by examiner

*Primary Examiner*—David H. Willse
(74) *Attorney, Agent, or Firm*—Browdy and Neimark, PLLC

(57) ABSTRACT

In a tibial component comprising an anchor portion for being fixed in bone and a tray for a sliding plate of polyethylene, the tibial component cooperating with a femoral component which rests on the sliding plate by curved articulation surfaces, it is provided that the sliding plate (1) has an attachment (2) which extends inside the anchor portion (5) of the tibial plateau component (4) and which, distally of the tibial plateau component, is non-rotatably joined to the anchor portion (5) by positive fit.

4 Claims, 2 Drawing Sheets

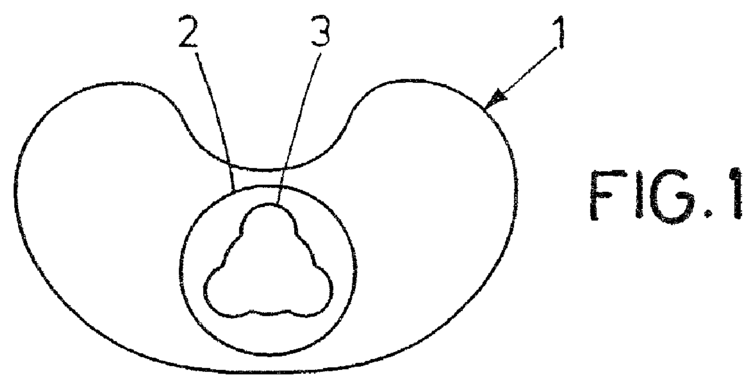
FIG. 1
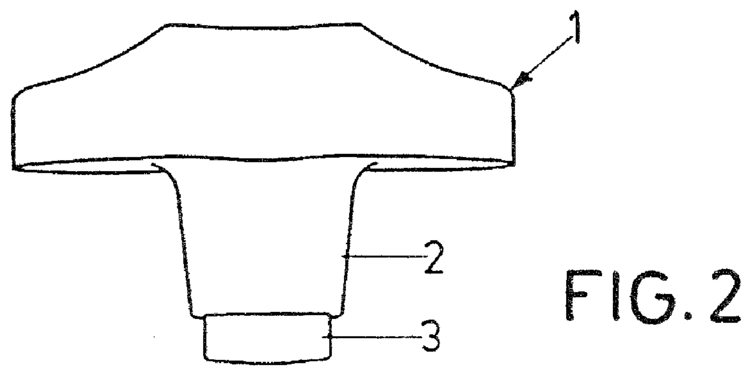
FIG. 2
| Femoral component rests on plate (1) |
|---|
FIG. 2A FIG. 3
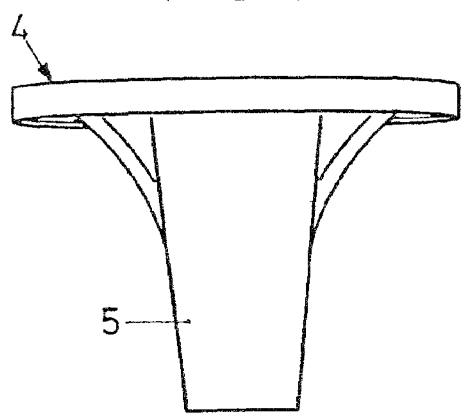
FIG. 4
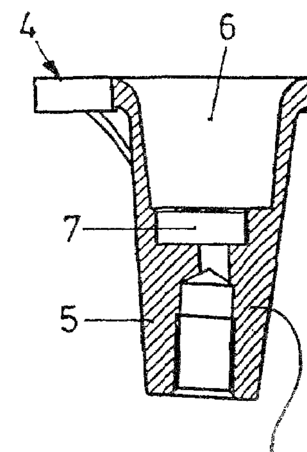
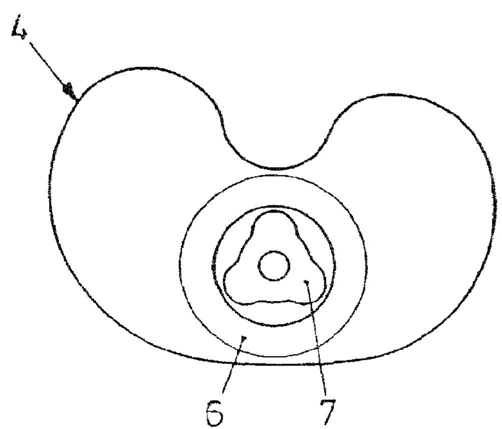
FIG. 5

TIBIA COMPONENT AND SLIDING PLATE OF A KNEE-JOINT ENDOPROSTHESIS

BACKGROUND OF THE INVENTION

1. Technical Field of the Invention

The invention relates to a tibial component which comprises an anchor portion for being fixed in bone; and to a tray for a sliding plate of polyethylene, the tibial component cooperating with a femoral component which rests on the sliding plate by curved articulation surfaces.

2. Prior Art

A knee joint endoprosthesis of the generic type has been described for example in P 41 02 509 A1.

Fundamentally, it is the object of a knee joint replacement to re-establish the function of the joint as far as possible by an endoprosthesis. In doing so, special consideration must be reserved for the kinematics and biomechanics involved and their principle of sliding-rolling motions. A knee joint prosthesis must be able to copy such motions and to absorb the strain by flexion, extension and rotation without any damages to the bone bearing and capsular ligament system.

To this end, endoprostheses have been known in which the tibial plateau component and femoral component are coupled, and endoprostheses of the generic type in which there is no such coupling. These bi-condylar prostheses make use of concepts that allow a selection of varying degrees of freedom in the motion of the polyethylene sliding components in relation to the tibial components. They include rigidly fixed sliding plates, rotating platforms, or platforms rotating by a translatory degree of freedom (anterior-posterior), and freely floating platforms. Given today's operating-room conditions, substantial competitive advantages reside in a reduced number of instruments and implants and in as free as possible an implementation of intraoperative decisions, these decisions including individually optimal compromises between mobility and stability. A fixed polyethylene sliding plate on which the femoral component rest offers maximal joint stability, a freely floating plate —preferably used where stable ligaments are available —permits a maximum of mobility.

Shaping the bi-condylar femoral and sliding component on which the femoral component rests must allow for the fact that highly congruent medial and lateral articulation surfaces will reduce the pressure load on polyethylene by offering an enlarged bearing area, but may restrict the degrees of freedom of the natural sliding-rolling motion of the joint of axial tibial rotation, this leading to high shearing forces and torsional stresses in a fixed sliding component. Undesired consequences consist in premature implant loosening in addition to high local strain, deformation and wear of the polyethylene sliding component.

OBJECT AND SUMMARY OF THE INVENTION

It is an object of the invention to embody a modular concept which enables polyethylene sliding plates on which a femoral component rests that are compatible with one another and have varying degrees of mobility to be placed on one and the same tibial plateau so that the number of tibial plateau components that must be kept available in the operating room can be reduced substantially. Moreover, use is intended to be made of the advantage of highly mating congruency in shape of the femoral and sliding component on which it rests, however accompanied with a reduction of the rotational forces that occur in this combination.

According to the invention, this object is attained by a sliding plate of high congruency with the femoral component having an attachment which extends inside the anchor portion of the tibial component and which, distally of the tibial component, is joined to the anchor portion non-rotatably and by positive fit.

As compared to the conventional way of rotary-motion securing directly to the tibial component etc., this distal displacement by some centimeters, as accomplished by the design according to the invention, produces a transfer of the occurring rotary motion on to the polyethylene sliding plate by the femoral component in such a way that local peak loads accompanied with high polyethylene wear are avoided, nevertheless enabling different sliding plates of correspondingly varying degrees of mobility simply to be simultaneously inserted intraoperatively.

As a result of the compatibility of these sliding plates with the tibial plateau component, in particular of the tray 4 and the anchor portion 5, the design according to the invention offers the possibility of modular assembly, which is accompanied with numerous advantages.

As mentioned above, the clinical acceptance of knee joint systems is decisively affected by the freedom of intraoperative decisions and fall-back on intraoperative options in addition to a reduced number of implants and instruments. Selection and use of the sliding plate belongs to the last steps in a surgical process prior to suturing. The function of flexion and extension of the entire knee joint is examined, above all involving the ligaments that provide for joint stability. In this stage, the embodiment according to the invention enables joint designs to be differentiated, varying between fixed systems, rotating mobility, anterior-posterior and rotating mobility (even multidirectional), as well as floating and rotating mobility.

For example the following typical operative situation is conceivable:

The femoral and tibial component are implanted and fixed (with or without cement). The implant system according to the invention offers a surgeon the possibility still to decide freely on the type of sliding plate he wants to implant. This is ensured by the distal displacement of the rotary-motion securing mechanism according to the invention. Distinct advantages reside in a reduced time of operation, gentle treatment of the bony bearing of the implant and bony area of contact as well as in saving a tibial component that can no longer be used. As compared to this, in prior art systems, the tibial component must still be replaced upon change-over from a mobile to a fixed sliding plate or vice versa.

Another essential advantage according to the invention resides in that, upon revision, the fixed femoral and tibial components can be left in the bone, with only the sliding plate on which the femoral component rests having to be replaced in dependence on the respective ligament situation. Removing a fixed and ingrown tibial component, which has been indispensable in prior art systems, is accompanied with quite a loss of healthy bone.

In keeping with another embodiment of the invention, provision can in particular be made for the anchor portion to have a distal recess of non-circular cross-sectional shape and the attachment of the sliding plate to have an end portion of corresponding outer contour, this end portion engaging with the non-circular recess by positive fit.

Preferably the non-circular recess has an approximately triangular basic shape with rounded corners, which helps preclude any peak stresses and attain reliable rotary-motion securing.

In keeping with another embodiment, it can be provided that the anchor portion of the tibial component inside comprises a non-circular positive surface contour which engages with a non-circular negative surface contour of the attachment of the sliding plate.

Another embodiment provides for non-rotatable connection by positive fit, in which the respective positive and negative surface contours of the sliding plate and the tibial plateau component are eccentric of the recess and the attachment. In this embodiment, surface contours are conceivable, featuring circular as well as non-circular engagement by positive fit.

In all the embodiments, provision can be made for metal reinforcements extending axially of the attachment of the sliding plate, by which to avoid shear of the polyethylene. The metal reinforcements may have a circular or non-circular cross-sectional shape.

BRIEF DESCRIPTION OF THE DRAWINGS

Details of the invention will become apparent from the ensuing description of a preferred embodiment, taken in conjunction with the drawing, in which FIG. 1 is a view from below of the polyethylene sliding plate and anchor portion;

FIG. 2 is a side view of the sliding plate and anchor portion;

FIG. 2A denotes femoral component which rests on the plate of FIG. 1.

FIG. 3 is a side view of the tibial plateau component;

FIG. 4 is a longitudinal view of the tibial plateau component; and

FIG. 5 is a plan view of the tibial plateau component in an implanted condition.

DETAILED DESCRIPTION OF THE PREEFERRED EMBODIMENT OF THE INVENTION

A sliding plate 1 of polyethylene seen in FIGS. 1 and 2 has a reniform basic shape, with an attachment 2 extending downwards which has an end portion 3 of triangular basic shape with rounded corners as seen in FIG. 1.

The tray 4 seen in FIGS. 3 to 5 is equipped with an anchor portion 5 which extends downwards, having an recess 6 that mates the shape of the attachment 2 of the sliding plate 1.

The bottom side of the recess 6 is provided with a recess 7 of smaller diameter which has a triangular basic shape with rounded corners and an outer contour that corresponds to the outer contour of the end portion 3.

When the sliding plate 1 seen in FIGS. 1 and 2 is inserted by its attachment 2 first into the recess 6, the end portion 3 engages with the recess 7 by positive fit so that a non-rotatable connection is produced.

Correspondingly it is possible to apply sliding plates 1 of varying degrees of mobility, using one and the same tibial plateau component 4.

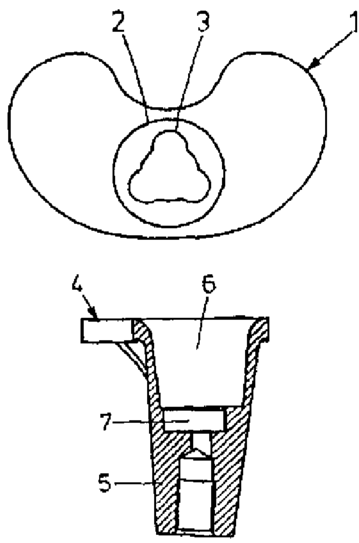

The invention claimed is:

1. A knee joint endoprosthesis, comprising:

a tibial component having an anchor portion (5) and a tray (4) on an upper end of the anchor portion adapted to be fixed to bone;

a femoral component adapted to be fixed to bone;

a polyethylene plate (1) having an attachment (2) formed as a unit with the plate (1);

the polyethylene plate (1) and attachment (2) made to consist of a polyethylene of ultrahigh molecular weight and/or a cross-linked polyethylene;

wherein the plate (1) is located between the femoral component and tibial component so that the femoral component rests and articulates on the polyethylene plate (1) by curved surfaces;

wherein the anchor portion (5) has a recess (7) having a non-circular cross-sectional shape spaced apart below the tray (4);

wherein said attachment (2) extends down inside the anchor portion (5) of the tibial component;

wherein a free end portion (3) of the attachment (2) is non-rotatably fixed by an outer contour on the free end portion (3) of the attachment (2) that corresponds to and engages in the non-circular recess (7) of the anchor portion (5) to provide a positive fit that precludes rotation of the free end portion (3) in the recess (7); and wherein the positive fit results in avoidance of local peak loads and high polyethylene wear.

2. The tibial component and plate according to claim 1, wherein the non-circular recess (7) has an approximately triangular basic shape with rounded corners.

3. The tibial component and plate according to claim 1, wherein the attachment (2) has metal reinforcements extending axially on the attachment to eliminate the shear of the polyethylene from which the attachment consists.

4. The tibial component and plate according to claim 1, wherein different plates having varying degrees of mobility can be selected for use with an already implanted tibial component.

* * * * *

UNITED STATES PATENT AND TRADEMARK OFFICE
CERTIFICATE OF CORRECTION

PATENT NO. : 7,470,289 B2
APPLICATION NO. : 10/514493
DATED : December 30, 2008
INVENTOR(S) : Peter Brehm It is certified that error appears in the above-identified patent and that said Letters Patent is hereby corrected as shown below:

The Title page, showing an illustrative figure, should be deleted and substitute therefor the attached title page.

In the patent on the first sheet of drawings, replace Figure 2 with the following corrected Fig. 2 with an insertion of a reference block diagram pointing to reference numeral 2, which reads --Metal Reinforcements--:

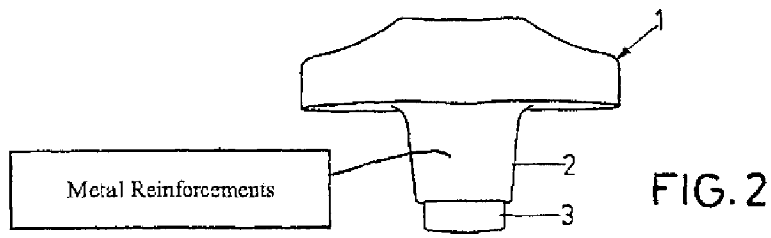

In the patent on the second sheet of the drawings, replace Figure 4 with the following corrected Fig. 4 with the deletion of the reference block diagram which reads “Metal Reinforcements”:

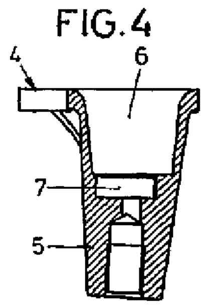

Signed and Sealed this

Seventh Day of July, 2009

JOHN DOLL
*Acting Director of the United States Patent and Trademark Office*

(12) United States Patent
Brehm

(10) Patent No.: US 7,470,289 B2
(45) Date of Patent: Dec. 30, 2008

(54) TIBIA COMPONENT AND SLIDING PLATE OF A KNEE-JOINT ENDOPROSTHESIS

(76) Inventor: Peter Brehm, Am Mühlberg 34, 91085 Weisendorf (DE)

( * ) Notice: Subject to any disclaimer, the term of this patent is extended or adjusted under 35 U.S.C. 154(b) by 477 days.

(21) Appl. No.: 10/514,493

(22) PCT Filed: May 12, 2003

(86) PCT No.: PCT/EP03/04936

§ 371 (c)(1), (2), (4) Date: Nov. 15, 2004

(87) PCT Pub. No.: WO03/094804

PCT Pub. Date: Nov. 20, 2003

(65) Prior Publication Data

US 2005/0222686 A1 Oct. 6, 2005

(30) Foreign Application Priority Data

May 14, 2002 (DE) ................................ 102 21 272

(51) Int. Cl.
*A61F 2/38* (2006.01)

(52) U.S. Cl. ................................ 623/20.15; 623/20.32

(58) Field of Classification Search .............. 623/20.15, 623/20.19, 20.21, 20.28, 20.29, 20.32, 20.33, 623/20.34, 23.46
See application file for complete search history.

(56) References Cited

U.S. PATENT DOCUMENTS 5,489,311 A 2/1996 Cipolletti
6,053,945 A * 4/2000 O'Neil et al. ............ 623/20.32
6,090,144 A 7/2000 Letot et al.
6,099,570 A * 8/2000 Livet et al. .............. 623/20.21

FOREIGN PATENT DOCUMENTS

| | | | |
|---|---|---|---|
| DE | 41 02 509 | A1 | 7/1992 |
| EP | 0 294 298 | B1 * | 5/1991 |
| EP | 0 838 204 | A | 4/1998 |
| EP | 0 904 748 | A | 3/1999 |
| FR | 2 278 389 | A | 11/1997 |

* cited by examiner

*Primary Examiner*—David H. Willse
(74) *Attorney, Agent, or Firm*—Browdy and Neimark, PLLC

(57) ABSTRACT

In a tibial component comprising an anchor portion for being fixed in bone and a tray for a sliding plate of polyethylene, the tibial component cooperating with a femoral component which rests on the sliding plate by curved articulation surfaces, it is provided that the sliding plate (1) has an attachment (2) which extends inside the anchor portion (5) of the tibial plateau component (4) and which, distally of the tibial plateau component, is non-rotatably joined to the anchor portion (5) by positive fit.

4 Claims, 2 Drawing Sheets